United States Patent
Tartarin et al.

(10) Patent No.: US 9,410,002 B2
(45) Date of Patent: Aug. 9, 2016

(54) AQUEOUS EMULSION COMPOSITION OF ORGANIC PEROXIDE

(71) Applicant: ARKEMA FRANCE, Colombes (FR)

(72) Inventors: Isabelle Tartarin, Oullins (FR); Jacques Cochet, Chanas (FR); Albert Blum, Weissenhorn (DE)

(73) Assignee: ARKEMA FRANCE, Colombes (FR)

(*) Notice: Subject to any disclaimer, the term of this patent is extended or adjusted under 35 U.S.C. 154(b) by 0 days.

(21) Appl. No.: 14/429,674

(22) PCT Filed: Sep. 6, 2013

(86) PCT No.: PCT/FR2013/052060
§ 371 (c)(1),
(2) Date: Mar. 19, 2015

(87) PCT Pub. No.: WO2014/044949
PCT Pub. Date: Mar. 27, 2014

(65) Prior Publication Data
US 2015/0218293 A1 Aug. 6, 2015

(30) Foreign Application Priority Data
Sep. 21, 2012 (FR) ..................................... 12 58874

(51) Int. Cl.
| | | |
|---|---|---|
| *C08K 5/14* | (2006.01) | |
| *C08L 29/04* | (2006.01) | |
| *C08F 114/06* | (2006.01) | |
| *C08F 4/32* | (2006.01) | |
| *C07C 407/00* | (2006.01) | |
| *C07C 409/00* | (2006.01) | |

(52) U.S. Cl.
CPC ................. *C08F 114/06* (2013.01); *C08F 4/32* (2013.01); *C08K 5/14* (2013.01); *C08L 29/04* (2013.01); *C07C 407/006* (2013.01); *C07C 409/00* (2013.01)

(58) Field of Classification Search
CPC .......................... C07C 407/006; C07C 407/00
USPC .......................................... 252/186.1, 186.42
See application file for complete search history.

(56) References Cited

U.S. PATENT DOCUMENTS

| | | | | |
|---|---|---|---|---|
| 3,988,261 A | | 10/1976 | Barter et al. | |
| 4,245,744 A | * | 1/1981 | Daniels ................. | D04H 1/641 206/210 |
| 4,359,427 A | * | 11/1982 | Gardner ................ | C07C 407/00 558/264 |
| 4,396,527 A | * | 8/1983 | Matsuyama .............. | C08F 4/32 252/186.23 |
| 4,515,929 A | * | 5/1985 | Tang .................... | C07C 407/006 252/186.26 |
| 6,350,835 B1 | * | 2/2002 | O ............................. | C08F 4/34 252/182.28 |
| 7,214,329 B2 | * | 5/2007 | O ........................ | C07C 407/006 252/182.13 |
| 7,446,074 B2 | * | 11/2008 | De Jong ............. | C07C 407/006 502/160 |
| 8,846,832 B2 | * | 9/2014 | de Jong .................... | C08F 4/38 252/186.26 |
| 2012/0184691 A1 | | 7/2012 | De Jong et al. | |

FOREIGN PATENT DOCUMENTS

| | | | | | |
|---|---|---|---|---|---|
| EP | 1 564 225 A1 | * | 8/2005 | ................ | C08F 4/32 |
| JP | 62-86005 A | * | 4/1987 | ................ | C08F 4/32 |
| JP | 2001-064312 | * | 3/2001 | ................ | C08F 4/32 |
| JP | 2001-064312 A | | 3/2001 | | |
| WO | WO 99/05101 A1 | | 2/1999 | | |
| WO | WO 03/095500 A1 | | 11/2003 | | |
| WO | WO 2011/015567 A2 | * | 2/2011 | ............ | C07C 407/00 |

OTHER PUBLICATIONS

Grimaldi et al. (EP 1 564 225) Aug. 17, 2005; translation in English.*
International Search Report (PCT/ISA/210) mailed on Oct. 22, 2013, by the French Patent Office as the International Searching Authority for International Application No. PCT/FR2013/052060.
Jean-Paul Canselier et al., "Procédés d'émulsification—Mécanisme de formation des emulsions (Emulsification processes—Mechanism of Formation of Emulsions)", Techniques de l'Ingénieur, pp. J2 152-1-J2 152-12 (pp. 1-12), publication of Jun. 10, 2004.

* cited by examiner

*Primary Examiner* — Rip A Lee
(74) *Attorney, Agent, or Firm* — Buchanan Ingersoll & Rooney P.C.

(57) ABSTRACT

An aqueous emulsion composition of organic peroxide, including from 10 to 65% by weight of one or a plurality of organic peroxides, from 2 to 25% by weight of at least one antifreeze agent, from 0.01 to 10% by weight of at least one emulsifying agent, optionally at least one additive, water, of which the quantity is defined in order to form the remainder of the total composition (100%), wherein the emulsifying agent is a colloid agent of a polyvinyl acetate having a degree of hydrolysis greater than 80% and a viscosity, measured in solution in water at 4% by weight at 20° C., less than or equal to 5 mPa·s, said viscosity being measured with a Brookfield RVT viscometer, needle no. 3, 20 rpm, in accordance with the ISO 2555 standard. Also, to the method of preparing same and the use thereof.

14 Claims, No Drawings

AQUEOUS EMULSION COMPOSITION OF ORGANIC PEROXIDE

FIELD OF THE INVENTION

A subject matter of the invention is an aqueous organic peroxide composition which is liquid at storage temperature and which can be used for the polymerization or the copolymerization of ethylenically unsaturated monomers and in particular of vinyl chloride. The invention relates more particularly to an aqueous composition comprising an emulsifier based on polyvinyl acetate having a high degree of hydrolysis and a low viscosity in solution in water.

Particular precautions in terms of safety have to be taken during the maintenance and handling of organic peroxides. Organic peroxides are packaged in aqueous emulsion form. The presence of water, as heat-transfer fluid, makes it possible to absorb and to dissipate the energy generated in the event of possible decompositions of the peroxides. Furthermore, these emulsions comprise an antifreeze which makes it possible to keep the emulsion in liquid form at temperatures of less than −10° C., generally of less than −20° C. These negative temperatures make it possible to prevent the uncontrolled decomposition of the peroxides during storage and transportation operations.

An organic peroxide emulsion is composed of peroxide droplets stabilized by an emulsifier. Over time, the emulsion destabilizes and the mean size of the peroxide droplets increases. The increase in the size of the droplets can bring about phase separation. According to the minimum technical criteria, a peroxide emulsion is regarded as satisfactory if the mean size of the droplets does not exceed 20 μm (micrometer). A mean size of the droplets of less than 10 μm, more advantageously of less than 5 μm, is generally required, as well as a maximum size not exceeding 20 μm.

In addition to the safety considerations due to this phenomenon of destabilization, the use of a nonhomogeneous organic peroxide emulsion as polymerization initiator in a vinyl monomer emulsion or suspension can bring about a nonhomogeneity in the final product. This nonhomogeneity is generally characterized by poorly gelled polymer particles during implementation in the molten state (fish eyes, hard grains). In point of fact, the presence of hard grains opacifies the polymer material. These stability considerations are thus very important for the applications where the transparency of the final product is essential, in particular for medical applications.

Thus, the peroxide droplets (by agglomeration of the peroxide or peroxides present in the emulsion, in particular after a certain period of time) of an organic peroxide emulsion have to have a low mean size, to have a homogeneous and monomodal size distribution and to be stable over time. In particular, the maximum diameter of these droplets should not exceed 20 μm. This is because phenomena of agglomeration or of enlargement of peroxide droplets can result in complete or partial phase separation of the emulsion.

The stages of unloading the emulsion into intermediate storage silos, of pumping and of introducing a peroxide emulsion into a polymerization reactor are important stages for the quality of the polymer obtained and the reliability of the polymerization process. These handling stages have to be carried out as rapidly as possible. To do this, it is crucial for the peroxide emulsion to exhibit a low viscosity so that the flow of the emulsion is facilitated to the maximum. At a given temperature, the viscosity of this type of emulsion varies in particular as a function of the shear rate. It decreases when the shear rate increases and becomes stabilized for rate values generally of greater than 100 $s^{-1}$. Thus, an organic peroxide emulsion must have a maximum dynamic viscosity of 1000 mPa·s (milliPascal·second) at low temperature, typically of the order of −10° C., for a shear rate of 100 $s^{-1}$. The dynamic viscosity measurements are carried out using coaxial cylinders which create the shearing, for example according to the standard DIN 53019.

In point of fact, a person skilled in the art knows that, for this type of emulsion, to attempt to reduce the size of the droplets contributes to increasing the viscosity (see section 1.4 of the paper by J. P. Canselier and M. Poux, "Procédés d'émulsification—Mécanisme de formation des émulsions" [Emulsification Processes—Mechanism of Formation of the Emulsions], Techniques de l'Ingénieur J2 152, pp. 1-12, publication of Jun. 10, 2004).

Thus, to achieve these two main objectives simultaneously is a major difficulty for a person skilled in the art due to the conflicting choices which he is driven to envisage.

STATE OF THE ART

The use of partially hydrolyzed polyvinyl acetate (PVA) is widely described in the literature as colloid agent for the stabilization of organic peroxide emulsion, such as in the documents EP 0 032 757 and U.S. Pat. No. 3,988,261.

A nonhydrolyzed PVA is insoluble in water. The document WO 99/05101 discloses the use of PVA having a degree of hydrolysis of between 45% and 68% for aqueous peroxyester emulsions. This document specifies that PVAs having a degree of hydrolysis of greater than 68% produce excessively viscous emulsions which are unstable, the size of the droplets of which varies in excessively great manner after a certain storage time, which cannot prevent the risks generated during the decomposition of the peroxides and which are unsuitable for the applications targeted above.

The document WO 03/095500 discloses the use of PVA as protective colloid for aqueous peroxydicarbonate or diacyl emulsions, having a degree of hydrolysis within a broad range between 45% and 80%, more specifically, as disclosed in the examples, around a value of the degree of hydrolysis of 65%.

Thus, the state of the art teaches that, on the one hand, in an aqueous organic peroxide emulsion, the use of polyvinyl acetates having a degree of hydrolysis of less than a maximum of 70% produces peroxyester, peroxydicarbonate and diacyl peroxide emulsions which satisfy the stringent conditions of viscosity and of stability essential to the handling of such emulsions and that, on the other hand, above this limit with regard to the degree of hydrolysis of the PVA, the use of the latter is not under any circumstances appropriate in such an emulsion.

BRIEF DESCRIPTION OF THE INVENTION

Surprisingly, the applicant company has discovered, contradicting the teachings of the prior art, that emulsifiers based on polyvinyl acetate having a high degree of hydrolysis stabilize peroxide emulsions and meet the conditions required relating to the size of the peroxide droplets and the viscosity of the emulsion. These characteristics are fulfilled during the highly particular combination of characteristics specific to polyvinyl acetate, namely a high degree of hydrolysis with a very low intrinsic viscosity.

The present invention thus relates to an aqueous organic peroxide emulsion composition comprising:
  from 10% to 65% by weight of one or more organic peroxides,
  from 2% to 25% by weight of at least one antifreeze agent, from 0.01% to 10% by weight of at least one emulsifying agent,
optionally at least one additive,
water, the amount of which is determined so as to form the remainder of the total composition (100%),
characterized in that the emulsifying agent is a colloid agent consisting of a polyvinyl acetate having a degree of hydrolysis of greater than 80% and a viscosity, measured in solution in water at 4% by weight at 20° C., of less than or equal to 5 mPa·s, said viscosity being measured with a Brookfield RVT viscometer, spindle No. 3, 20 rpm (revolutions per minute), according to the standard ISO 2555.

Other characteristics or embodiments of the invention are presented below:
  preferably, the viscosity of the partially hydrolyzed polyvinyl acetate, measured in solution in water at 4% by weight at 20° C., is less than or equal to 3 mPa·s (always under the same measurement conditions);
  according to one possibility offered by the invention, the partially hydrolyzed polyvinyl acetate is modified in its acetate groups by metal salts, preferably chosen from sulfonates and sodium carboxylates;
  advantageously, the composition according to the invention comprises a second emulsifying agent consisting of a nonionic surfactant of ethoxylated fatty acid type, such as ethoxylated fatty acid mono-, di- or triglycerides or ethoxylated vegetable oils, ethoxylated fatty alcohol type or a block copolymer comprising at least one alkylene oxide block type;
  preferably, this second emulsifying agent consists of an ethoxylated castor oil;
  advantageously, the degree of hydrolysis of the polyvinyl acetate is greater than 85%, more preferably between 86% and 89%;
  preferably, the organic peroxide or peroxides are chosen from peroxyesters, peroxydicarbonates and/or diacyl peroxides;
  according to a distinctive feature specific to the invention, the composition exhibits a viscosity defined by a flow time of less than 200 seconds, preferably of less than 100 seconds, said flow time being measured at the temperature of 5° C. according to the standard DIN 53211. For further details, the standard DIN 53211 is in this instance characterized by a diameter of the viscosity cup of 4 mm; the dynamic viscosity is less than 1000 mPa·s and is measured at −10° C. for a shear rate of 100 s$^{-1}$ using a Haake VT550 Viscotester according to the standard DIN 53019;
  likewise, according to a characteristic specific to the invention, the composition comprises a plurality of droplets formed of peroxide in that the mean size ($d_{50}$) of said droplets is less than 10 μm (micrometer), preferably less than 5 μm, and the maximum size ($d_{100}$) of the droplets is less than 20 μm;
  advantageously, the composition according to the invention comprises more than 30% by weight of one or more organic peroxides, preferably more than 45% by weight;
  advantageously, the polyvinyl acetate is present at between 1% and 5% by weight, preferably between 0.5% and 3%.

The invention exhibits the following advantages and thus makes it possible to obtain:
  an emulsion exhibiting a low mean droplet size with a homogeneous and monomodal size distribution,
  an emulsion comprising a mean droplet size ($d_{50}$) of less than 10 μm after production or during storage at −20° C. for at least 12 weeks. The maximum size ($d_{100}$) does not exceed 20 μm,
  an emulsion compatible with the polymerization of ethylenically unsaturated derivatives and in particular of vinyl monomers, such as the vinyl chloride monomer,
  a liquid emulsion having a very low viscosity which allows a very short flow time.

The present invention also relates to a process for the preparation of the composition according to any one of the preceding claims, characterized in that it comprises the successive stages of:
  dispersion of the antifreeze agent, optionally at least said additive and also the colloid agent in water, in order to obtain a homogeneous aqueous phase, then
  the peroxide is added to the aqueous phase, and
  the mixture thus formed is emulsified during an emulsification stage at a temperature of less than 5° C., preferably of less than −5° C.

Finally, the invention relates to the use of the composition targeted above in the polymerization or the copolymerization of ethylenically unsaturated monomers. Preferably, these ethylenically unsaturated monomers comprise vinyl chloride.

The organic peroxide emulsion according to the present invention can be used in applications such as the polymerization of acrylic monomers, reactions for modifying polymers, crosslinking reactions, bulk polymerization reactions and curing processes as used in unsaturated polyester resins.

The description which will follow is given solely by way of illustration and without implied limitation.

DETAILED DESCRIPTION OF THE INVENTION

The invention relates to compositions formed of concentrated organic peroxide in emulsion, said organic peroxide being present at a concentration of 10% to 65%, preferably of greater than 30% and more preferably of greater than 45% by weight of the emulsion and being chosen from peroxyesters, peroxydicarbonates and diacyl peroxides.

The preferred peroxides among the peroxyesters are α-cumyl peroxyneodecanoate, α-cumyl peroxyneoheptanoate, 2,4,4-trimethylpent-2-yl peroxyneodecanoate, 3-hydroxy-1,1-dimethylbutyl peroxyneodecanoate, 3-hydroxy-1,1-dimethylbutyl peroxyneoheptanoate, tert-amyl peroxypivalate, tert-butyl peroxypivalate, tert-butyl peroxyneoheptanoate, 2,5-dimethyl-2,5-di(2-ethylhexanoyl-peroxy) hexane, tert-amyl peroxy-2-ethylhexanoate, tert-butyl peroxy-2-ethylhexanoate, 1,1,3,3-tetramethylbutyl peroxy-2-ethylhexanoate, 3-hydroxy-1,1-dimethylbutyl peroxy-2-ethylhexanoate, tert-butyl peroxyisobutyrate and their mixtures.

The preferred peroxides among the peroxydicarbonates are di(sec-butyl) peroxydicarbonate, dibutyl peroxydicarbonate, diisopropyl peroxydicarbonate, di(2-ethylhexyl) peroxydicarbonate, bis(3-methoxybutyl) peroxydicarbonate, bis(isobutyl) peroxydicarbonate, dineopentyl peroxydicarbonate, bis(1-methylheptyl) peroxydicarbonate, bis[2-(2-methoxyethoxy)ethyl]peroxydicarbonate, bis(3-methoxy-3-methylbutyl) peroxydicarbonate, bis(2-ethoxyethyl) peroxydicarbonate and their mixtures.

The preferred peroxides among the diacyl peroxides are diisobutyroyl peroxide, di(3,5,5-trimethylhexanoyl) peroxide, di(2-ethylhexanoyl) peroxide, di(2-ethylbutanoyl) peroxide and also asymmetric peroxides, such as isobutyroyl octanoyl peroxide, isobutyroyl decanoyl peroxide, isobutyroyl lauroyl peroxide, 2-ethylbutanoyl decanoyl peroxide or 2-ethylhexanoyl lauroyl peroxide, and their mixtures.

In order to be able to be stored at temperatures of less than −10° C., preferably of less than −20° C., the composition according to the invention comprises an antifreeze or more particularly a mixture of antifreeze.

As regards the antifreeze agent, mention may be made, for example, of monools, diols and triols, such as methanol, ethanol, ethylene glycol, isopropanol, n-propanol, propane-1,2-diol, propane-1,3-diol, glycerol, butan-1-ol, butan-2-ol, butane-1,3-diol, butane-1,4-diol and their mixtures, these mixtures comprising at least two of the antifreeze agents listed above, one of light alcohol type and the other of heavy alcohol type, advantageously a mixture of methanol and propane-1,2-diol.

The emulsifier according to the invention is a polyvinyl acetate having a degree of hydrolysis of greater than 80% and a viscosity, in solution in water at 4% by weight at 20° C., of less than 10 mPa·s, preferably of less than 5 mPa·s.

As regards the partially hydrolyzed polyvinyl acetate, it can consist of Alcotex® 8804, Mowiol® 3-85 or Gohseran® L3266, all well known to a person skilled in the art.

It is not departing from the scope of the invention when a mixture of partially hydrolyzed polyvinyl acetate according to the present invention is used as emulsifier.

According to one embodiment, the emulsifier according to the invention, namely the partially hydrolyzed polyvinyl acetate, is modified in its acetate groups by metal salts preferably chosen from sulfonates and sodium carboxylates.

A mixture of unmodified polyvinyl acetate with a modified polyvinyl acetate according to the present invention can be used as emulsifying mixture for the stabilization of organic peroxide emulsion.

The PVAs modified in their acetate groups are preferably chosen from Gohseran® L 3266, well known to a person skilled in the art.

A second nonionic emulsifier can be used in combination with the partially hydrolyzed polyvinyl acetate, modified or unmodified, according to the invention and consists of a nonionic surfactant of ethoxylate fatty acid type, which are ethoxylated mono-, di- or triglyceride derivatives or ethoxylated vegetable oils, ethoxylated fatty alcohol type or block copolymer comprising at least one alkylene oxide block type. The ethoxylated vegetable oils are in particular (hydrogenated or nonhydrogenated) ethoxylated castor oil comprising from 20 to 40 mol of ethylene oxide per mole of ricinoleic acid; commercial examples are in particular Remcopal® 20, Remcopal® R4097 and Remcopal® RH4090, which are well known to a person skilled in the art.

According to the invention, the second emulsifier, a nonionic surfactant of ethoxylated castor oil type, is present at a concentration in the invention of between 0.01 and 3% by weight, preferably of between 0.5 and 2% by weight.

The emulsion according to the invention can also comprise one or more additives intended to provide the final thermoplastic composition with specific properties/characteristics. These additives will ideally be present for the final polymerization or copolymerization.

Thus, as regards the additive, it can be chosen from antioxidants; UV protection agents; processing aids having the role of improving the final appearance during its use, such as fatty amides, stearic acid and its salts, ethylenebisstearamide or fluoropolymers; antifogging agents; antiblocking agents, such as silica or talc; fillers, such as calcium carbonate and nanofillers, such as, for example, clays; coupling agents, such as silanes; crosslinking agents, such as peroxides; antistatic agents; nucleating agents; pigments; dyes; plasticizers; viscosity reducers and flame-retardant additives, such as aluminum or magnesium hydroxides.

The liquid aqueous organic peroxide emulsion of the present invention can optionally comprise additives including pH-adjusting agents, such as phosphate and citrate buffers, chelating agents, biocides, for example fungicides, antiozonants, antioxidants, degradation inhibitors, blowing agents and mold-release agents. The emulsion can also comprise additives normally used to stabilize the organic peroxide or to delay its decomposition, such as phlegmatizers (isododecane, mineral oil) and hydroperoxides.

These additives can be added in the amounts normally used and known to a person skilled in the art. These additives are generally used in contents of between 10 ppm and 10 000 ppm by weight, with respect to the weight of final polymer or copolymer. The plasticizers, the viscosity reducers and the flame-retardant additives can reach amounts far above 10 000 ppm.

The invention also relates to a process for the preparation of the emulsion described above, characterized in that the antifreeze agent, optionally one or more additives and also at least one emulsifier are dispersed in water, in order to obtain a homogeneous aqueous phase, and then the peroxide is added to said aqueous phase, the combined mixture subsequently being emulsified during an emulsification stage at a temperature of less than 5° C., so as to limit the premature decomposition of the peroxide, preferably of less than −5° Celsius.

Apart from the specific successive stages of the process for the preparation of the composition according to the invention, the preparation of the emulsion does not differ in any way from the techniques and devices well known to a person skilled in the art. The temperature at which emulsion is prepared is not critical but it must be sufficiently low to prevent a significant degree of decomposition, the result of which would be a loss in the assay. The temperature chosen depends essentially on the organic peroxide or peroxides. Furthermore, in order to prepare the aqueous emulsions, deionized water or distilled water is conventionally used.

The preparation process comprises a stage of emulsification with a mixer having a high shear rate in order to as best as possible divide and/or homogenize the peroxide in the aqueous phase. Mention may be made, by way of example, of mechanically rotating anchor and paddle stirrers, helical stirrers, that is to say one or more stirrers fitted to a common shaft, turbine stirrers, that is to say those comprising stationary baffles on the mixing vessel or in a position adjacent to the stirring members. Use may also be made of colloid mills and homogenizers. According to one implementational characteristic, the process according to the invention is characterized in that an ultrasonic mixer or a rotor-stator mixer is used.

Subsequent to the preparation of the emulsion according to the invention, the stages of pumping and introducing the emulsions into a polymerization reactor had to be carried out as quickly as possible. The peroxide emulsions must have a low viscosity.

Thus, the organic peroxide emulsions according to the invention exhibit a dynamic viscosity of range at −10° C., 100 $s^{-1}$, of less than 1000 mPa·s, preferably of less than 700 mPa·s, immediately after production. The viscosity measurements are carried out, for example, according to the standard DIN 53019 with a device of Haake Viscotester VT550 type at −10° C. and for a shear rate of 100 $s^{-1}$.

Their flowability or flow time, measured by a flow cup technique, is less than 200 seconds, preferably less than 100 seconds (standard DIN 53211, carried out with a diameter of a cup of 4 mm at a temperature of 5° C.).

The subsequent stages of polymerization or copolymerization are not, in the context of the present invention, different from those of the prior art. The polymerization of the vinyl chloride monomer is carried out in suspension at an initiation temperature of between 45 and 70° C.

The invention also relates to the use of the emulsion defined above in the polymerization or copolymerization of ethylenically unsaturated monomers. A homopolymer is obtained by polymerization when just one ethylenically unsaturated monomer is polymerized. A copolymer is obtained by polymerization when at least two ethylenically unsaturated monomers are polymerized. It is understood that the monomers are capable of polymerizing with one another.

Mention may be made, as ethylenically unsaturated monomers of acrylates, vinyl esters, vinyl halide monomers, vinyl ethers, aromatic vinyl compounds, such as styrene, or butadiene and preferably vinyl chloride.

Preparation of the Formulations of the Test Compositions:

The comparative PVAs, numbered 1, 2, 3, 5, 7 and 8, and the PVAs according to the invention, numbered 4, 6 and 9, act as emulsifiers in emulsions 1 to 16 (emulsions 11 to 16 use the PVAs previously numbered 4, 6 and 9) and are prepared according to the same procedure.

The aqueous phase containing the PVA, the antifreeze agent and the water is stirred between 500 and 1000 rpm (revolutions per minute) and maintained at a temperature of −5° C. (Celsius). The organic peroxide is gradually added to the reactor containing this water/PVA/antifreeze agent mixture. Stirring is maintained at 2000 rpm for three minutes. The combined mixture is subsequently stirred vigorously at 9500 rpm for two minutes using an UltraTurrax type S-25N 18G device of rotor-stator type and then at 1000 rpm for one minute while stirring with a paddle. Each emulsion amounts to 200 grams in total.

Tests Carried Out:

The dynamic viscosity measurements are carried out using a viscometer of Haake Viscotester VT550 type. The measurement device is the SV-DIN 53019, referring to the standard DIN 53019. The measurement is carried out using coaxial cylinders which create the shearing. Between 5 and 10 ml (milliliters) of emulsion is introduced into the measurement chamber maintained at −10° C. The values given in the examples below correspond to a shear rate of $100\ s^{-1}$ and are expressed in mPa·s. The accuracy of the measurement is ±10% of the value shown.

The measurements of flow time are carried out using flow cups of DIN 53211 type (diameter of the viscosity cup: 4 mm). The measurement is carried out on 100 g of emulsion after conditioning at a temperature of +5° C. The measurements of flow time are expressed in seconds and the accuracy is ±10% of the value shown.

The size of the droplets ($d_{100}$ and $d_{50}$) is determined by conventional means using the light diffraction technique. The term $d_{100}$ corresponds to the diameter such that 100% of the volume of the sample of organic peroxide droplets in the aqueous emulsion has a diameter of less than $d_{100}$ and the term $d_{50}$ corresponds to the mean diameter such that 50% of the volume of the droplets of organic peroxide in the aqueous emulsion has a diameter of less than $d_{50}$. The measurements are carried out using a Malvern Master Sizer 2000® device at ambient temperature. The droplet sizes $d_{50}$ or $d_{100}$ are given to ±0.5 μm.

Starting Materials of the Test Compositions:

Mainly two types/families of emulsions were prepared in order to carry out the tests which make it possible to characterize the compositions according to the prior art and according to the invention.

The first emulsion consists of 60% by weight di(2-ethylhexyl) peroxydicarbonate and comprises:
an antifreeze system which is a mixture of alcohols in a 20/80 ratio by weight of propylene glycol/methanol, with an overall concentration of 14%;
a water/antifreeze ratio of 64/36 by weight;
a content of di(2-ethylhexyl) peroxydicarbonate of 60% by weight. The di(2-ethylhexyl) peroxydicarbonate is Luperox® 223 from Arkema with a purity of 97%;
a content of partially hydrolyzed polyvinyl acetate (PVA) of 1.2% by weight;
the remainder is distilled water.

The second emulsion consists of 50% by weight tert-butyl peroxyneodecanoate and comprises:
an antifreeze system which is a mixture of alcohols in a 40/60 ratio by weight of propylene glycol/methanol, with an overall concentration of 16%;
a water/antifreeze ratio of 67/33 by weight;
a content of tert-butyl peroxyneodecanoate of 50% by weight. The tert-butyl peroxyneodecanoate is Luperox® 10 from Arkema with a purity of 97%;
a content of partially hydrolyzed polyvinyl acetate (PVA) of 1.2% by weight;
the remainder is distilled water.

Characterizations of the PVAs:

The characteristics of the comparative PVAs and of the PVAs according to the invention are presented in table 1:

TABLE 1

|  | Degree of polymerization | Viscosity (mPa · s) | Degree of hydrolysis (%) |
|---|---|---|---|
| PVA 1 | 800 | 5.6-6.6 | 72-73 |
| PVA 2 | 1630 | 36-42 | 78.5-81.5 |
| PVA 3 | 2560 | 44-52 | 78.5-81.5 |
| PVA 4 | 360 | 3.5-4.5 | 88 |
| PVA 5 | 2440 | 45-49 | 86.7-88.7 |
| PVA 6 | 300 | 3 | 85-90 |
| PVA 7 | Unknown | 6-7 | 86-90 |
| PVA 8 | 1700 | 20-26 | 85-90 |
| PVA 9 | Unknown | 2.5 | 87 |
| PVA 10 | 1100 | 2.2 | 42-45 |

The viscosity is measured at 4% in water at 20° C. (Brookfield RVT viscosity, spindle No. 3, 20 rpm).

PVA 9 is a PVA modified by sulfonate functional groups.

It is clearly found that only PVA No. 4, PVA No. 6 and PVA No. 9 correspond to the criteria (low viscosity and high degree of hydrolysis) defined in the invention. To make reading easier, in the table and in the following tables, the PVAs or the emulsions according to the invention are presented in bold.

A second emulsifier of nonionic surfactant type of ethoxylated castor oil type of Remcopal® 20 (R20) type is added at 1% by weight to emulsion 10 (with PVA according to the invention, more specifically PVA No. 4 of the above table), emulsion 11 (with PVA according to the invention, more specifically PVA No. 6 of the above table) and emulsion 15 (with PVA according to the invention, more specifically PVA No. 6 of the above table).

Emulsions:

Emulsions 1 to 11 and 16 correspond to di(2-ethylhexyl) peroxydicarbonate peroxide emulsions and emulsions 12 to 15 correspond to tert-butyl peroxyneodecanoate peroxide emulsions, and are characterized in tables 2 and 3:

TABLE 2

|  | Emulsions 1-11, 16 | Emulsions 12-15 |
|---|---|---|
| Di(2-ethylhexyl) peroxydicarbonate, % | 60.0 |  |
| tert-Butyl peroxyneodecanoate, % |  | 50.0 |
| Methanol, % | 11.2 | 9.6 |

TABLE 2-continued

|  | Emulsions 1-11, 16 | Emulsions 12-15 |
|---|---|---|
| Propylene glycol, % | 2.8 | 6.4 |
| Surfactant, % | 1.2 | 1.2 |
| Water, % | 24.8 | 32.8 |

TABLE 3

|  | $d_{50}$ (μm) | $d_{100}$ (μm) | Viscosity (mPa·s) | Flow time (s) |
|---|---|---|---|---|
| Emulsion 1 (PVA 1) | 4 | 12 | 1100 | 145 |
| Emulsion 2 (PVA 2) | 7.1 | 112 | 2200 | >300 |
| Emulsion 3 (PVA 3) | 7.4 | 141 | 1650 | >300 |
| Emulsion 4 (PVA 4) | 3.9 | 13.3 | 790 | 92 |
| Emulsion 5 (PVA 5) | 8.6 | 100 | 3090 | >300 |
| Emulsion 6 (PVA 6) | 3.4 | 12.6 | 670 | 72 |
| Emulsion 7 (PVA 7) | 4.1 | 19.9 | 1020 | 133 |
| Emulsion 8 (PVA 8) | 5.2 | 30.2 | 3250 | >300 |
| Emulsion 9 (PVA 9) | 2.7 | 7.6 | 580 | 66 |
| Emulsion 10 (PVA 4/R20) | 1.8 | 4.0 | 580 | 83 |
| Emulsion 11 (PVA 6/R20) | 1.8 | 4.0 | 530 | 63 |
| Emulsion 12 (PVA 1) | 3.3 | 8.7 | 608 | 64 |
| Emulsion 13 (PVA 9) | 3.3 | 8.7 | 190 | 26 |
| Emulsion 14 (PVA 6) | 3.8 | 11.1 | 363 | 38 |
| Emulsion 15 (PVA 6/R20) | 2.2 | 5.0 | 297 | 37 |
| Emulsion 16 (PVA 10) | 4.0 | 12.6 | 570 | 67 |

It will be noted that, in this instance, only emulsions Nos. 10, 11, 13, 14 and 15 are in accordance with the invention.

PVAs having very high viscosities do not make it possible to obtain fluid emulsions with short flow times and sufficiently fine droplet sizes.

The more the viscosity of the PVA is low and less than 5 mPa·s, the more the emulsion meets the performance criteria in terms of fluidity.

The viscosities of the emulsions comprising a nonionic surfactant of ethoxylated castor oil type (Remcopal® 20 or denoted R20 above) are lower than those comprising only a PVA. This is because addition of a nonionic surfactant, such as an ethoxylated castor oil of Remcopal® 20 type, to a PVA emulsifier according to the invention contributes to reducing the viscosity of the corresponding emulsion. Thus, the viscosity of the emulsion obtained is then close to that achieved with a modified PVA, for example modified by sulfonate functional groups. Moreover, in addition to reducing the viscosity, the addition of a second emulsifier according to the invention contributes to reducing the mean size of the organic peroxide droplets.

Generally, a 50% by weight concentrated peroxyester emulsion is slightly more fluid than a 60% by weight concentrated peroxydicarbonate emulsion. On the other hand, the emulsions stabilized by the PVAs according to the invention are more fluid than those comprising a comparative PVA (according to the prior art). In the case of the peresters, the addition of a nonionic surfactant of ethoxylated castor oil type again contributes to reducing the viscosity of the emulsion while lowering the size of the droplets. It should be noted that the tests presented here do not include the diacyl peroxides but the results obtained with regard to the peroxyesters and the peroxydicarbonates allow similar results to be envisaged with the diacyl peroxides. This is because the diacyl peroxides have formed the subject of preliminary tests as satisfactory as those obtained with the peroxyesters and the peroxydicarbonates.

The emulsions produced with different comparative PVAs and PVAs according to the invention are stored at a temperature of −20° C. for several months. The characteristics of the different emulsions are measured after different storage times. The results are presented in table 4:

TABLE 4

|  | Emulsion 1 (PVA1) | Emulsion 6 (PVA 6) | Emulsion 11 (PVA 6/ R20) | Emulsion 9 (PVA 9) | Emulsion 16 (PVA 10) |
|---|---|---|---|---|---|
| $d_{50}$ (μm) |  |  |  |  |  |
| t = 0 | 3.3 | 3.4 | 1.8 | 2.7 | 4.0 |
| t = 4 weeks | 3.6 | / | / | 3.1 | 4.2 |
| t = 8 weeks | 3.7 | 3.8 | 2.2 | 3.2 | 4.2 |
| t = 12 weeks | 3.8 | 4 | 2.3 | 3.3 | 4.4 |
| $d_{100}$ (μm) |  |  |  |  |  |
| t = 0 | 10.0 | 12.6 | 4.0 | 7.6 | 12.6 |
| t = 4 weeks | 10.0 | / | / | 8.7 | 13.2 |
| t = 8 weeks | 10.0 | 14.8 | 5.8 | 8.7 | 15.1 |
| t = 12 weeks | 13.2 | 15.1 | 5.8 | 8.7 | 15.1 |
| Viscosity (mPa·s) |  |  |  |  |  |
| t = 0 | 1100 | 670 | 530 | 580 | 570 |
| t = 4 weeks | 1180 | / | / | / | 560 |
| t = 8 weeks | 1170 | 730 | 430 | 500 | 630 |
| t = 12 weeks | 1170 | 750 | 400 | / | 670 |
| Flow time (s) |  |  |  |  |  |
| t = 0 | 145 | 72 | 63 | 66 | 67 |
| t = 4 weeks | 170 | / | / | 56 | 70 |
| t = 8 weeks | 171 | 90 | 59 | 52 | 77 |
| t = 12 weeks | 198 | 95 | 57 | / | 85 |

The emulsions comprising a PVA according to the invention make it possible to retain the good properties of the emulsion after a minimum of 12 weeks of storage. The viscosities of the emulsions remain very fluid and less than 1000 mPa·s (measured according to the standard DIN 53019 with a Haake Viscotester VT550 at −10° C. and for a shear rate of 100 s$^{-1}$), the flow times remain less than 150 seconds and preferably 100 seconds and the maximum sizes $d_{100}$ do not exceed 20 μm (micrometers).

Generally, only the aqueous peroxide emulsion compositions according to the invention make it possible to solve the two major technical problems, namely the enlarging of the peroxide droplets over time, or in other words the stability of the emulsion, and the viscosity under cold conditions of the emulsion, which is often excessively high, resulting in particular in unsatisfactory flow times.

The invention claimed is:

1. An aqueous organic peroxide emulsion composition comprising:
   from 10% to 65% by weight of one or more organic peroxides,
   from 2% to 25% by weight of at least one antifreeze agent,
   from 0.01% to 10% by weight of at least one emulsifying agent,
   optionally at least one additive,
   water, the amount of which is determined so as to form the remainder of the total composition (100%),
   wherein the at least one emulsifying agent is a colloid agent consisting of a polyvinyl acetate having a degree of hydrolysis of greater than 80% and a viscosity, measured in solution in water at 4% by weight at 20° C., of less than or equal to 3 mPa·s, said viscosity being measured with a Brookfield RVT viscometer, spindle No. 3, 20 rpm, according to the standard ISO 2555.

2. The composition as claimed in claim 1, wherein the partially hydrolyzed polyvinyl acetate is modified in its acetate groups by metal salts.

3. The composition as claimed in claim 1, wherein the at least one emulsifying agent comprises a second emulsifying agent consisting of a nonionic surfactant of ethoxylated fatty acid type.

4. The composition as claimed in claim 3, wherein the second emulsifying agent consists of an ethoxylated castor oil.

5. The composition as claimed in claim 1, wherein the degree of hydrolysis of the polyvinyl acetate is greater than 85%.

6. The composition as claimed in claim 1, wherein the organic peroxide or peroxides are chosen from peroxyesters, peroxydicarbonates and/or diacyl peroxides.

7. The composition as claimed in claim 1, wherein the composition exhibits a viscosity defined by a flow time of less than 200 seconds, said flow time being measured at the temperature of 5° C. according to the standard DIN 53211.

8. The composition as claimed in claim 1, wherein the composition comprises a plurality of droplets formed of peroxide in that the mean size ($d_{50}$) of said droplets is less than 10 μm (micrometer), and the maximum size ($d_{100}$) of the droplets is less than 20 μm.

9. The composition as claimed in claim 1, wherein the composition comprises more than 30% by weight of one or more organic peroxides.

10. The composition as claimed in claim 1, wherein the polyvinyl acetate is present at between 1% and 5% by weight.

11. A process for the preparation of the composition according to claim 1, wherein the process comprises the successive stages of:

dispersion of the antifreeze agent, optionally at least said additive and also the colloid agent in water, in order to obtain a homogeneous aqueous phase, then the peroxide is added to the aqueous phase, and the mixture thus formed is emulsified during an emulsification stage at a temperature of less than 5° C.

12. A method for polymerization or copolymerization of ethylenically unsaturated monomers comprising adding the composition as claimed in claim 1 to a solution comprising the ethylenically unsaturated monomers.

13. The method as claimed in claim 12, wherein the ethylenically unsaturated monomers comprise vinyl chloride.

14. An aqueous organic peroxide emulsion composition comprising:

from 10% to 65% by weight of one or more organic peroxides, from 2% to 25% by weight of at least one antifreeze agent, from 0.01% to 10% by weight of at least one emulsifying agent, optionally at least one additive, water, the amount of which is determined so as to form the remainder of the total composition (100%), wherein the at least one emulsifying agent is a colloid agent consisting of a polyvinyl acetate having a degree of hydrolysis of greater than 80% and a viscosity, measured in solution in water at 4% by weight at 20° C., of less than or equal to 5 mPa·s, said viscosity being measured with a Brookfield RVT viscometer, spindle No. 3, 20 rpm, according to the standard ISO 2555; and wherein the composition comprises a second emulsifying agent consisting of an ethoxylated castor oil.

\* \* \* \* \*